(12) United States Patent
Linblad et al.

(10) Patent No.: US 10,988,431 B2
(45) Date of Patent: Apr. 27, 2021

(54) UPGRADING LIGNOCELLULOSIC OR CARBOHYDRATE MATERIAL

(71) Applicant: Neste Oyj, Espoo (FI)

(72) Inventors: Marina Linblad, Porvoo (FI); Mats Käldström, Porvoo (FI); Susanna Wallenius, Porvoo (FI); Sören Sundblom, Porvoo (FI); Maaria Seläntaus, Porvoo (FI); Elias Ikonen, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 16/474,786

(22) PCT Filed: Dec. 22, 2017

(86) PCT No.: PCT/EP2017/084400
§ 371 (c)(1),
(2) Date: Jun. 28, 2019

(87) PCT Pub. No.: WO2018/122169
PCT Pub. Date: Jul. 5, 2018

(65) Prior Publication Data
US 2019/0352248 A1  Nov. 21, 2019

(30) Foreign Application Priority Data
Dec. 30, 2016 (EP) .................... 16207467

(51) Int. Cl.
C07C 51/353 (2006.01)
B01J 23/10 (2006.01)
(Continued)

(52) U.S. Cl.
CPC ............. *C07C 51/353* (2013.01); *B01J 23/10* (2013.01); *B01J 23/78* (2013.01); *C07C 51/367* (2013.01); *C10G 3/50* (2013.01)

(58) Field of Classification Search
CPC ....... C07C 51/353; C07C 51/367; C10G 3/00; B01J 23/10; B01J 23/78
See application file for complete search history.

(56) References Cited

U.S. PATENT DOCUMENTS

| 2006/0135793 A1 | 6/2006 | Blessing et al. |
| 2016/0221912 A1* | 8/2016 | Myllyoja ............ C07C 51/367 |

(Continued)

FOREIGN PATENT DOCUMENTS

| CN | 105283463 A | 1/2016 |
| CN | 105837429 A | 8/2016 |

(Continued)

OTHER PUBLICATIONS

International Search Report (PCT/ISA/210) dated Feb. 19, 2018, by the European Patent Office as the International Searching Authority for International Application No. PCT/EP2017/084400.

(Continued)

*Primary Examiner* — Youngsul Jeong
(74) *Attorney, Agent, or Firm* — Buchanan Ingersoll & Rooney PC

(57) ABSTRACT

The present disclosure relates to a method for upgrading lignocellulosic material carbohydrates and/or carbohydrate derivatives by dimerisation and/or oligomerisation using specific catalysts and to the use of the upgraded products.

30 Claims, 2 Drawing Sheets

(51) Int. Cl.
    *B01J 23/78*     (2006.01)
    *C07C 51/367*     (2006.01)
    *C10G 3/00*     (2006.01)

(56) References Cited

U.S. PATENT DOCUMENTS

| | | |
|---|---|---|
| 2016/0221914 A1 | 8/2016 | Myllyoja et al. |
| 2016/0264876 A1 | 9/2016 | Mascal et al. |
| 2017/0008864 A1 | 1/2017 | Lindblad et al. |
| 2017/0073294 A1 | 3/2017 | Myllyoja et al. |

FOREIGN PATENT DOCUMENTS

| | | | |
|---|---|---|---|
| CN | 106103661 A | 11/2016 | |
| WO | 2015144856 A1 | 10/2015 | |
| WO | WO-2015144856 A1 * | 10/2015 | ............ B01J 23/883 |

OTHER PUBLICATIONS

Written Opinion (PCT/ISA/237) dated Feb. 19, 2018, by the European Patent Office as the International Searching Authority for International Application No. PCT/EP2017/084400.

Shen, Wenqin, et al., "Liquid phase aldol condensation reactions with MgO—$ZrO_2$ and shape-selective nitrogen-substituted NaY", Applied Catalysis A: General, vol. 392, No. 1-2, Jan. 29, 2011, pp. 57-68.

European Search Report for EP 16207467.8 dated Jun. 14, 2017 (7 pges).

Office Action dated Mar. 3, 2021, by the Chinese Patent Office in corresponding Chinese Patent Application No. 201780076604.6. (8 pages).

* cited by examiner

UPGRADING LIGNOCELLULOSIC OR CARBOHYDRATE MATERIAL

TECHNICAL FIELD

The present invention relates to upgrading lignocellulosic and/or carbohydrate material, specifically to a method of upgrading the material by dimerisation and/or oligomerisation, followed by optional hydrogenation and/or purification/separation. Further, the present invention relates to the use of a dimer/oligomer obtainable by the method of the invention as an intermediate for the production of fuel and/or chemicals or of a hydrogenated product thereof as a fuel component.

TECHNICAL BACKGROUND

U.S. Pat. No. 8,629,310 B2 discloses upgrading of lignocellulosic oxygenate base material, such as γ-valerolactone (GVL), comprising the steps of hydrogenating the oxygenate base material, followed by condensing the hydrogenated base material.

WO 2015/144856 A1 discloses condensation of levulinic acid (LA) in the presence of a solid acid catalyst system.

EP 3050868 A1 discloses condensation of levulinic acid (LA) in the presence of water and a base catalyst which may comprise sodium hydroxide or potassium hydroxide.

SUMMARY OF THE INVENTION

Figure 1:
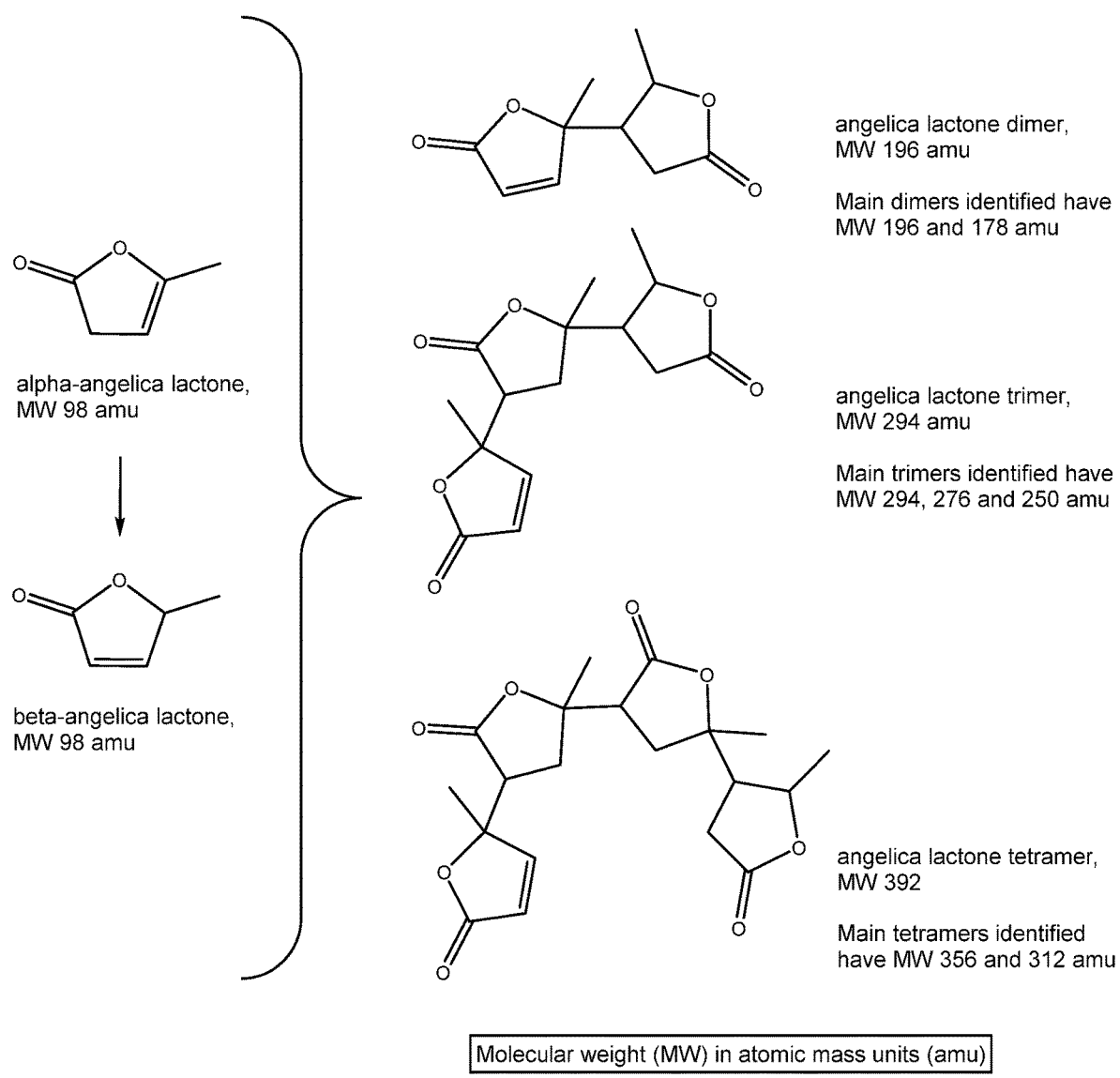
FIG. 1 is a reaction scheme showing an example of angelica lactone (AL) dimer and oligomer reaction products obtainable by the present invention.
Figure 2:
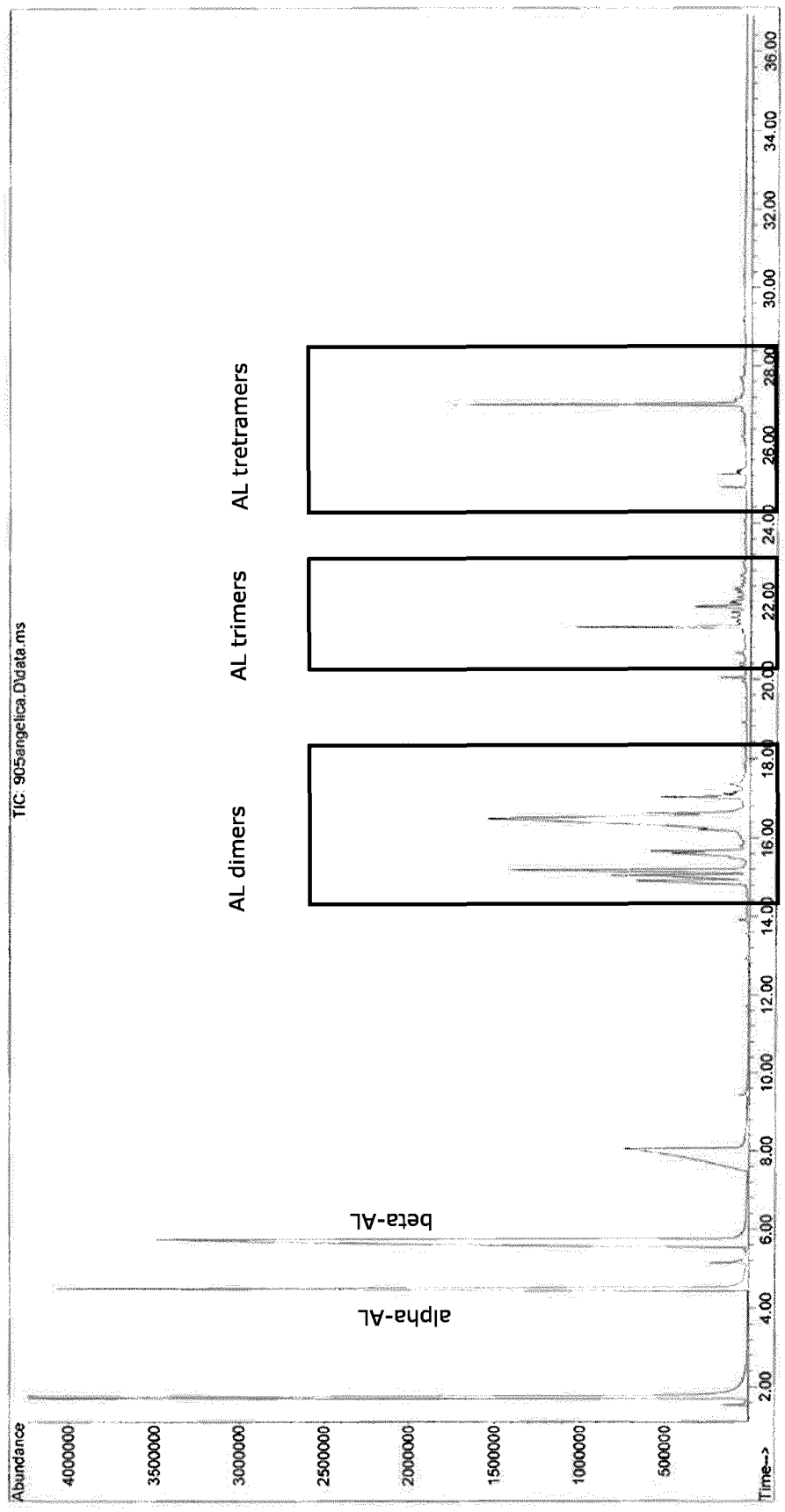
FIG. 2 is a GC-MS plot of a product obtained by dimerising/oligomerising AL using the method of the present invention.

The present invention is defined in the independent claims. Further beneficial embodiments are set forth in the dependent claims. Specifically, the present invention relates to one or more of the following items:
1. A method for upgrading carbohydrates, carbohydrate derivatives or lignocellulosic material, the method comprising
providing a feedstock comprising carbohydrates, carbohydrate derivatives or lignocellulosic material, wherein the lignocellulosic material, carbohydrates or carbohydrate derivatives comprises *angelica* lactone (AL), and
dimerising and/or oligomerising the carbohydrates, carbohydrate derivatives or lignocellulosic material in the presence of a heterogeneous catalyst, wherein
the lignocellulosic material is levulinic acid, an ester of levulinic acid and/or a dehydration product of levulinic acid,
the heterogeneous catalyst is an inorganic catalyst comprising an alkali metal compound and/or an alkaline earth metal compound and at least one further metal compound.
2. The method according to item 1, wherein the heterogeneous catalyst is a supported catalyst.
3. The method according to item 1 or 2, wherein the heterogeneous catalyst is a catalyst comprising the alkali metal compound and/or the alkaline earth metal compound on a support formed by the further metal compound, wherein the support is preferably formed by an oxide of the further metal.
4. The method according to item 1 or 2, wherein the heterogeneous catalyst is a catalyst comprising an oxide of the alkali metal and/or an oxide of the alkaline earth metal on a support formed by an oxide of the further metal.
5. The method according to item 1, wherein the heterogeneous catalyst is a catalyst comprising the alkali metal compound and/or the alkaline earth metal compound in the form of a mixed compound, in which all compounds are preferably in oxide form.
Here, the term "mixed compound" refers to a mixture on a chemical level, i.e. not to a blend. When all compounds are in oxide form, the "mixed compound" is thus a mixed oxide.
6. The method according to any one of items 1 to 5, wherein the metal constituting the alkali metal compound and/or an alkaline earth metal compound is at least one selected from the group consisting of Li, Na, K, Mg and Ca.
7. The method according to any one of items 1 to 6, wherein the further metal constituting the further metal compound is at least one selected from the group consisting of Al, Si, Sc, Ti, V, Y, Zr, Nb, Mo, La, Ce, Hf, Ta and W.
8. The method according to any one of items 1 to 7, wherein the heterogeneous catalyst comprises potassium oxide/titania ($K_2O/TiO_2$) or magnesia/zirconia ($MgO/ZrO_2$).
9. The method according to any one of items 1 to 8, wherein the step of dimerising/oligomerising is carried out at a reaction temperature in the range of 30° C. to 220° C., preferably 40° C. or more, 45° C. or more or 50° C. or more, preferably 210° C. or less, 200° C. or less, 195° C. or less, 190° C. or less, 185° C. or less or 180° C. or less, further preferably in the range of 50° C. to 200° C. or 50° C. to 185° C.
10. The method according to any one of items 1 to 9, wherein the heterogeneous catalyst is an inorganic catalyst comprising an alkali metal compound and/or an alkaline earth metal compound and no further metal compound as the heterogeneous catalyst.
11. The method according to any one of items 1 to 10, wherein the alkaline metal compound and/or the alkaline earth metal compound is a metal oxide, nitride, carbonate and/or carbide.
12. The method according to any one of items 1 to 11, wherein the metal constituting the alkali metal compound and/or an alkaline earth metal compound is at least one selected from the group consisting of Na, K and Mg.
13. The method according to any one of items 1 to 6, wherein the further metal constituting the further metal compound is at least one selected from the group consisting of Al, Si, Ti, Zr and Ce.
14. The method according to any one of items 1 to 13, further comprising a hydrogenation step of hydrogenating the dimer/oligomer to obtain a hydrogenated product.
15. A use of the dimer/oligomer obtainable by the method according to any one of items 1 to 13 as an intermediate for the production of fuel and/or chemicals.
16. A use of the hydrogenated product obtainable by the method according to item 13 as a fuel component.

DETAILED DESCRIPTION OF THE INVENTION

The invention is now explained in detail with reference to specific embodiments. It is to be noted that any feature of the embodiments may be combined with any feature of another embodiment provided that such a combination does not result in a contradiction.

The present invention relates to a method for upgrading carbohydrates, carbohydrate derivatives or lignocellulosic material, the method comprising providing a feedstock comprising carbohydrates, carbohydrate derivatives or lignocellulosic material, and dimerising and/or oligomerising the carbohydrates, carbohydrate derivatives or lignocellulosic material in the presence of a heterogeneous catalyst, wherein the lignocellulosic material is levulinic acid, an ester of levulinic acid, a salt of levulinic acid and/or a dehydration product of levulinic acid, the heterogeneous catalyst is an inorganic catalyst comprising an alkali metal compound and/or an alkaline earth metal compound and at least one further metal compound.

In the present invention, the dimerisation/oligomerisation is preferably an oligomerisation. That is, the reaction results in the formation of at least oligomers. In the context of the present invention, oligomers are trimers or higher, specifically trimers, tetramers, pentamers or hexamers, preferably mainly (more than 50 area-% (GPC area) relative to all oligomers) trimers and tetramers. The oligomers may be homooligomers (constituted of one type of ketoacid) or heterooligomers/mixed oligomers (constituted of different types of reactants, e.g. two different ketoacids or three different ketoacids). In the case of mixed oligomers, the oligomer product may contain a mixture of different mixed oligomers. Specifically, the content of oligomers is preferably 10 area-% or more, 20 area-% or more, more preferably 25 area-% or more, 30 area-% or more, 35 area-% or more, 40 area-% or more, 45 area-% or more, 50 area-% or more, 55 area-% or more, 60 area-% or more, or 65 area-% or more relative to the sum of dimers and oligomers in the dimer/oligomer product. Since oligomers are a favourable product fraction (e.g. for fuel production, specifically diesel and/or jet fuel), it is preferably that the content thereof in the dimer/oligomer product is high. Unlike conventional methods, the method of the present invention is suited to achieve high relative amounts of oligomers, even at moderate temperature. Thus, the present method can produce oligomers while reducing the risk of side reactions, such as coke formation.

In the present invention, carbohydrates include any kinds of saccharides, such as monosaccharides, disaccharides, oligosaccharides, polysaccharides such as chitin. Specifically, carbohydrates of the present invention comprise sugars as well as starch and/or cellulose. The derivatives of carbohydrates include any derivatives having a saccharide base structure (or backbone), such as halides of saccharides, aminosaccharides, desoxysaccharides or esters, ethers or amides of saccharides. The derivatives of carbohydrates may also include any dehydration products from carbohydrates such as 5-hydroxymethylfurfural (HMF).

The levulinic acid, which is contained as a lignocellulosic material, carbohydrates or carbohydrate derivatives includes free acid (having a —COOH group) as well as salt forms thereof, preferably the free acid form. The salt of levulinic acid may be an alkali metal salt and/or an alkaline earth metal salt.

The ester of levulinic acid may be an alkyl ester (including branched, cyclic and/or substituted alkyl).

The dehydration product of levulinic acid comprises levulinic acid anhydride and/or a cyclic dehydration product of levulinic acid such as angelica lactone. Among the dehydration product, cyclic dehydration products are preferred, angelica lactone is more preferred and α-angelica lactone is most preferred. This explicitly applies to all embodiments of the present invention.

The alkali metal compound and alkaline earth metal compound may both be contained. Preferably only one out of these two is contained, most preferably the alkali metal compound.

The further metal of the further metal compound is neither an alkali metal nor an alkaline earth metal. The further metal compound may be provided as a support (sometimes referred to as carrier) of the alkali metal compound and/or the alkaline earth metal compound or in a mixed compound with an alkali metal compound and/or an alkaline earth metal compound. Mixed compound refers to a mixture on a chemical level. The catalyst may also be a composite in which an alkali metal compound and/or an alkaline earth metal compound are present as agglomerates chemically bound to a further metal compound.

The method of the present invention provides several benefits over the prior art. Specifically, due to the use of the heterogeneous catalyst comprising the two types of metal compounds, the dimerisation/oligomerisation can be achieved in high yields with good selectivity. Further, compared to conventional homogenous catalyst reactions, the method achieves lower catalyst loss while it is easier to separate the product from the catalyst.

In the present invention, the lignocellulosic material preferably comprises angelica lactone (AL). The angelica lactone may be alpha-angelica lactone (α-AL; 4-Hydroxy-3-pentenoic acid γ-lactone; IUPAC: 5-Methyl-2(3H)-furanone) or beta-angelica lactone (β-AL; 4-Hydroxy-2-pentenoic acid γ-lactone; IUPAC: 5-Methyl-2(5H)-furanone) or a mixture thereof. The lignocellulosic material particularly preferably comprises α-AL. Further the lignocellulosic material may comprise a mixture of AL and levulinic acid (LA). The experiments conducted by the inventors of the present invention have shown that AL, specifically α-AL, and LA can be readily dimerised and/or oligomerised using the method of the present invention.

The heterogeneous catalyst is preferably a catalyst comprising the alkali metal compound and/or the alkaline earth metal compound on a support (carrier) formed by the further metal compound, wherein the support is preferably formed by an oxide of the further metal. When the further metal compound is an oxide, it is preferable that the alkali metal compound and/or the alkaline earth metal compound is an oxide as well. Thus, the heterogeneous catalyst may be a catalyst comprising an oxide of the alkali metal and/or an oxide of the alkaline earth metal on a support formed by the oxide of the further metal. The further metal compound, preferably an oxide, may alternatively be provided in a mixed compound with the alkali metal compound and/or the alkaline earth metal compound, as explained above. Specifically, the heterogeneous catalyst may be a catalyst comprising the alkali metal compound and/or the alkaline earth metal compound in the form of a mixed compound, in which preferably all compounds are in oxide form. In the case of a mixed oxide, the mixed compound may be a mixed oxide of the further metal oxide and the oxide of the alkali metal and/or the oxide of the alkaline earth metal. Further, the catalyst may also be a composite.

Specifically, as long as at least the further metal compound and at least one of the alkali metal compound and the alkaline earth metal compound are in physical contact with each other, the effects of combining these compounds, namely the improved efficiency of the catalyst, can be achieved.

The metal constituting the alkali metal compound and/or an alkaline earth metal compound is preferably at least one selected from the group consisting of Li, Na, K, Mg and Ca, preferably at least one selected from the group consisting of Na, K and Mg. Catalysts comprising at least one of these metals in the alkaline (earth) metal compound have shown exceptional efficiency when used as a catalyst component in the method of the present invention.

The metal constituting the further metal compound is preferably at least one selected from the group consisting of Al, Si, Sc, Ti, V, Y, Zr, Nb, Mo, La, Ce, Hf, Ta and W, preferably at least one selected from the group consisting of Al, Si, Ti, Zr and Ce. These compounds, which are preferably provided as oxides, are particularly suited as carriers, mixed components and/or composite constituents when combined with the alkaline (earth) metal compound.

In an alternative approach, it is also possible to use only a compound, such as an oxide, nitride, carbonate and/or carbide, of an alkali metal and/or of an alkaline earth metal as the heterogeneous catalyst, i.e. even if no further metal compound is provided as a part of the catalyst.

Preferred combinations of the alkaline earth metal compound or the alkali metal compound and the further metal compound for use in the method of the present invention are as follows, wherein the term "Ox" refers to an oxide of the respective metal and the sign "/" refers to providing the respective compounds as a supported catalyst (the latter preferably being the support) or a mixed compound catalyst:

NaOx/AlOx; KOx/AlOx; MgOx/AlOx; NaOx/SiOx; KOx/SiOx; MgOx/SiOx; NaOx/TiOx; KOx/TiOx; MgOx/TiOx; NaOx/CeOx; KOx/CeOx; MgOx/CeOx; NaOx/ZrOx; KOx/ZrOx; MgOx/ZrOx, wherein KOx/TiOx and MgOx/ZrOx are particularly preferred.

Hydrotalcite ($Mg_6Al_2CO_3(OH)_{16}.4(H_2O)$) may be employed as a catalyst which comprises an alkaline earth metal (Mg) compound and a further metal (Al) compound in the form of a mixed compound.

A catalyst MgOx/ZrOx ($MgO/ZrO_2$) can be produced as shown in the Examples.

The heterogeneous catalyst may specifically be potassium oxide/titania ($K_2O/TiO_2$) or magnesia/zirconia ($MgO/ZrO_2$). In the case of these two combinations of alkali metal and/or alkaline earth metal compound (oxide) and other metal compound (oxide), exceptional synergistic interactions were found which were not at all expected from the individual compounds. Nevertheless, the other combinations of alkali metal and/or alkaline earth metal compound and other metal compound were found to be favourable as well.

The dimerisation/oligomerisation step is preferably carried out at a reaction temperature in the range of 30° C. to 220° C. The lower limit of the reaction temperature is preferably 40° C. or more, 45° C. or more or 50° C. or more. The upper limit of the reaction temperature is preferably 210° C. or less, 200° C. or less, 195° C. or less, 190° C. or less, 185° C. or less or 180° C. or less. The temperature in this step is preferably in the range of 50° C. to 200° C. or 50° C. to 185° C.

Furthermore, in the case of using an alkaline earth metal compound in the catalyst, the reaction temperature is preferably in the range of 30° C. to 150° C. The upper limit is preferably 140° C., 130° C., 120° C., 110° C., 100° C. or 90° C. The lower limit is preferably 35° C., 40° C., 45° C. or 50° C. Furthermore, in the case of using an alkali metal compound in the catalyst, the reaction temperature is preferably in the range of 110° C. to 220° C. The upper limit is preferably 210° C., 200° C., 195° C., 190° C. or 185° C. The lower limit is preferably 120° C., 130° C., 140° C., 150° C., 155° C. or 160° C.

Further, no hydrogenation is carried out in the dimerisation/oligomerisation step. This can be achieved by one or two or all of the following measures: (a) no hydrogen is supplied to the reactor in the dimerisation/oligomerisation step; (b) no catalyst having hydrogenating activity is present in the reactor in the dimerisation/oligomerisation step; (c) the reaction conditions (temperature and/or pressure, including partial pressure of individual gases) are adjusted such that no hydrogenation reaction occurs.

Using these conditions, high yield can be achieved at a relatively low temperature, which avoids the occurrence of undesired side-reactions. Moreover, using the catalyst of the present invention, a high oligomer (trimer and higher) content can be achieved even at low temperature.

The method of the present invention preferably further comprises a hydrogenation step of hydrogenating the dimer/oligomer to obtain a hydrogenated product.

The hydrogenation may be carried out by any conventional means using any conventional catalyst. The hydrogenation is preferably a hydrodeoxygenation reaction. More preferably, the hydrogenated product is a hydrocarbon composition, i.e. a composition comprising compounds constituted of only carbon atoms and hydrogen atoms, wherein minor amounts (up to 5 wt.-%, preferably at most 4 wt.-%, at most 3 wt.-%, at most 2 wt.-% or at most 1 wt.-%) of non-hydrocarbon compounds may be present as impurities.

The present invention further relates to a use of the dimer/oligomer (product) obtainable by the method above as an intermediate for the production of fuel and/or chemicals. The dimer and/or oligomer (the product of the method) may be used as they are (i.e. usually as a mixture/blend of compounds) or may be separated and/or purified before further use. The product is particularly suitable as an intermediate for chemical industry, e.g. for the production of fine chemicals or polymers, and as an intermediate for fuel industry. In the latter case, it is preferable to at least partly convert the product into a hydrocarbon product (hydrocarbon composition) by hydrogenation (hydrodeoxygenation). The present invention particularly provides the use of the hydrogenated product obtainable by the method described above as a fuel component. In this case, it may be preferable to separate the dimer products from the oligomer (trimer or higher oligomer) products before and/or after hydrogenation, preferably after hydrogenation.

The hydrogenated products may be used as fuel components for gasoline, jet or diesel fuel. In this respect, hydrogenated dimer products or products comprising mainly (more than 50 wt.-%, preferably more than 80 wt.-% or more than 90 wt.-%) dimers are preferably used as gasoline fuel components, while products comprising mainly (more than 50 wt.-%, preferably more than 80 wt.-% or more than 90 wt.-%) hydrogenated trimers and tetramers are preferably used as diesel fuel components, and products comprising mainly (more than 50 wt.-%, preferably more than 80 wt.-% or more than 90 wt.-%) hydrogenated dimers and trimers are preferably used as jet fuel components.

The reactor for carrying out the dimerisation/oligomerisation reaction may be a batch reactor or a flow type reactor. Further, the reactor for carrying out the hydrogenation reaction may be a batch reactor or a flow type reactor.

A solvent may be contained in the feedstock. Although the presence of a solvent is usually not necessary, the solvent may be contained in an amount of at most 60 wt.-%, at most 40 wt.-%, at most 20 wt.-%, at most 15 wt.-%, at most 10 wt.-% or at most 5 wt.-%, when the feedstock as a whole is considered as 100 wt.-%; the catalyst and an optional carrier gas is not considered as being part of the feedstock.

EXAMPLES

The present invention is further illustrated by way of Examples. However, it is to be noted that the invention is not intended to be limited to the exemplary embodiments presented in the Examples.

In the Examples, the product leaving the reactor was analysed by GC-MS (Gas Chromatography-Mass Spectrometry), HPLC (High Performance Liquid Chromatography) and GPC (Gel Permeation Chromatography).

Catalyst Synthesis Example

A catalyst was prepared in accordance with Wenqin Shenet. al., Appl. Catal. A 392 (2011) 57-68 as follows. 50.9 g of $Mg(NO_3)_2 \cdot 6H_2O$ and 4.04 g of $ZrO(NO_3)_2$ were diluted in 1 l of ion-exchanged water. A 25 wt.-% NaOH aqueous solution was added in drops to the solution and mixed until the pH of the mixture was 10. The resulting gel was left at room temperature for 72 h and then separated by vacuum filtration. The precipitate was washed with generous amounts of ion-exchanged water and dried in an oven at 120° C. overnight. Calcination was done in air flow (100 ml/min) at 300° C. for 3 h.

After disintegration, a $MgO/ZrO_2$ catalyst powder was obtained.

Example 1

A continuous flow-type tubular reactor was loaded with 4 g of $MgO/ZrO_2$ catalyst as produced above. The catalyst was dried under nitrogen flow (6 l/h) at 300° C. for one hour. Commercial α-AL was used as a feedstock at 70° C., 0.6 bar and WHSV 1.1 $h^{-1}$ under nitrogen flow (3 l/h).

The product was analysed by GPC.

The liquid product contained 20 area-% α-AL, 15 area-% dimers, 20 area-% oligomers and 45 area-% β-AL.

Example 2

The procedure of Example 1 was repeated while the temperature in the dimerisation/oligomerisation reaction was increased to 100° C. The product was analysed by GPC as in Example 1.

The liquid product contained 8 area-% α-AL, 29 area-% dimers, 24 area-% oligomers (10 area-% trimers, 14 area-% tetramers), 1 area-% heavy compounds (polymeric material) and 38 area-% β-AL.

Example 3

A continuous flow-type tubular reactor was loaded with 4 g of $K_2O/TiO_2$ catalyst. Commercial α-AL was used as a feedstock at 175° C., 2.0 bar and WHSV 0.5 $h^{-1}$ under nitrogen flow (3 l/h).

The product was analysed by GPC as in Example 1. The liquid product contained 19 area-% α-AL, 12 wt.-% dimers, 9 area-% oligomers and 60 area-% β-AL.

Example 4

The procedure of Example 1 was repeated while the WHSV was changed to 0.15 $h^{-1}$. The product was analysed by GPC as in Example 1.

The liquid product contained 6 area-% α-AL, 37 area-% dimers, 39 area-% oligomers and 18 area-% β-AL.

In all Examples, the catalyst showed long-term stability under the conditions used in the Examples. Further, as confirmed by the Examples, the method of the present invention provides a high selectivity for oligomers. Specifically, in accordance with the present invention, the selectivity to oligomers (preferably higher than C10) is preferably 5 wt.-% or more, more preferably 10 wt.-% or more, even more preferably 30 wt.-% or more, most preferably 40 wt.-% or more, relative to the sum of oligomers (trimers and higher) and dimers.

The invention claimed is:

1. A method for upgrading carbohydrates, carbohydrate derivatives or lignocellulosic material, the method comprising:
    providing a feedstock containing carbohydrates, carbohydrate derivatives or lignocellulosic material, wherein the carbohydrates, carbohydrate derivatives, or lignocellulosic material include(s) angelica lactone; and
    dimerising and oligomerising the carbohydrates, carbohydrate derivatives, or lignocellulosic material at a reaction temperature in a range of 30° C. to 195° C., in a presence of a heterogeneous catalyst to produce a dimer and oligomer product;
    wherein the oligomerising constitutes formation of trimers or higher and wherein the content of trimers or higher is 30 area-% or more in a Gel Permeation Chromatography (GPC) chromatogram relative to the sum of dimers and oligomers in the dimer and oligomer product,
    wherein the lignocellulosic material is levulinic acid, an ester of levulinic acid and/or a dehydration product of levulinic acid,
    wherein the heterogeneous catalyst is an inorganic catalyst containing an alkali metal compound and at least one further metal compound, or is an inorganic catalyst containing an alkali metal compound and an alkaline earth metal compound and at least one further metal compound, and
    wherein the further metal constituting the at least one further metal compound is at least one selected from the group consisting of Al, Si, Sc, Ti, V, Y, Zr, Nb, Mo, La, Ce, Hf, Ta and W.

2. The method according to claim 1, wherein the heterogeneous catalyst is a supported catalyst.

3. The method according to claim 2, wherein the heterogeneous catalyst is a catalyst comprising:
    the alkali metal compound and/or the alkaline earth metal compound on a support formed by the at least one further metal compound.

4. The method according to claim 3, wherein the support is formed by an oxide of the further metal.

5. The method according to claim 2, wherein the heterogeneous catalyst is a catalyst comprising:
    an oxide of the alkali metal and/or an oxide of the alkaline earth metal on a support formed by an oxide of the further metal.

6. The method according to claim 1, wherein the heterogeneous catalyst is a catalyst comprising:
    the alkali metal compound and/or the alkaline earth metal compound as a mixed compound.

7. The method according to claim 6, wherein all metal compounds of the catalyst are in oxide form.

8. The method according to claim 1, wherein a metal constituting the alkali metal compound and/or an alkaline earth metal compound is at least one selected from the group consisting of Li, Na, K, Mg and Ca.

9. The method according to claim 5, wherein the metal constituting the alkali metal compound and/or an alkaline earth metal compound is at least one selected from the group consisting of Li, Na, K, Mg and Ca.

10. The method according to claim 8, wherein the further metal constituting the at least one further metal compound is at least one selected from the group consisting of Al, Si, Sc, Ti, V, Y, Zr, Nb, Mo, La, Ce, Hf, Ta and W.

11. The method according to claim 9, wherein the further metal constituting the at least one further metal compound is at least one selected from the group consisting of Al, Si, Sc, Ti, V, Y, Zr, Nb, Mo, La, Ce, Hf, Ta and W.

12. The method according to claim 1, wherein the further metal constituting the at least one further metal compound is at least one selected from the group consisting of Al, Si, Ti, Zr and Ce.

13. The method according to claim 8, wherein the further metal constituting the at least one further metal compound is at least one selected from the group consisting of Al, Si, Ti, Zr and Ce.

14. The method according to claim 9, wherein the further metal constituting the at least one further metal compound is at least one selected from the group consisting of Al, Si, Ti, Zr and Ce.

15. The method according to claim 1, wherein the heterogeneous catalyst further comprises a compound selected from the group consisting of NaOx/AlOx; KOx/AlOx; MgOx/AlOx; NaOx/SiOx; KOx/SiOx; MgOx/SiOx; NaOx/TiOx; KOx/TiOx; MgOx/TiOx; NaOx/CeOx; KOx/CeOx; MgOx/CeOx; NaOx/ZrOx; KOx/ZrOx; and MgOx/ZrOx, wherein the term "Ox" refers to an oxide of a respective metal and a sign "/" refers to providing respective compounds as a supported catalyst, including being the support, or a mixed compound catalyst.

16. The method according to claim 15, wherein the heterogeneous catalyst further comprises a compound selected from the group consisting of KOx/TiOx and MgOx/ZrOx.

17. The method according to claim 1, wherein the heterogeneous catalyst further comprises: potassium oxide/titania ($K_2O/TiO_2$) or magnesia/zirconia ($MgO/ZrO_2$).

18. The method according to claim 1, wherein the reaction temperature is in a range of 30° C. to 190° C.

19. The method according to claim 1, wherein the reaction temperature is in a range of 30° C. to 185° C.

20. The method according to claim 15, wherein the reaction temperature is in a range of 30° C. to 180° C.

21. The method according to claim 16, wherein the reaction temperature is in a range of 30° C. to 150° C.

22. The method according to claim 17, wherein the reaction temperature is in a range of 30° C. to 140° C.

23. The method according to claim 18, wherein the reaction temperature is in a range of 30° C. to 130° C.

24. The method according to claim 1, wherein the reaction temperature is in a range of 50° C. to 185° C.

25. The method according to claim 1, wherein the heterogeneous catalyst is an inorganic catalyst comprising:
an alkali metal compound and an alkaline earth metal compound and one further metal compound as the heterogeneous catalyst.

26. The method according to claim 1, wherein the alkaline metal compound and/or the alkaline earth metal compound is a metal oxide, a metal nitride, a metal carbonate and/or a metal carbide.

27. The method according to claim 1, wherein the metal constituting the alkali metal compound and/or an alkaline earth metal compound is at least one selected from the group consisting of Na, K and Mg.

28. The method according to claim 1, comprising:
hydrogenating the dimer and oligomer product to obtain a hydrogenated product.

29. The method according to claim 1, comprising:
applying the dimer and oligomer product as an intermediate for producing fuel and/or chemicals.

30. The method according to claim 28, comprising:
providing the hydrogenated product as a fuel component.

* * * * *